(12) United States Patent
Kim

(10) Patent No.: US 10,390,863 B2
(45) Date of Patent: Aug. 27, 2019

(54) ROD CONNECTOR

(71) Applicant: KYUNGPOOK NATIONAL UNIVERSITY INDUSTRY-ACADEMIC COOPERATION FOUNDATION, Daegu (KR)

(72) Inventor: Kyoung Tae Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 15/780,167

(22) PCT Filed: Dec. 22, 2016

(86) PCT No.: PCT/KR2016/015081
§ 371 (c)(1),
(2) Date: May 30, 2018

(87) PCT Pub. No.: WO2017/116072
PCT Pub. Date: Jul. 6, 2017

(65) Prior Publication Data
US 2018/0360502 A1 Dec. 20, 2018

(30) Foreign Application Priority Data
Dec. 29, 2015 (KR) ........................ 10-2015-0188285

(51) Int. Cl.
*A61B 17/70* (2006.01)
*A61B 17/86* (2006.01)

(52) U.S. Cl.
CPC ...... *A61B 17/7049* (2013.01); *A61B 17/7001* (2013.01); *A61B 17/7052* (2013.01); *A61B 17/86* (2013.01)

(58) Field of Classification Search
CPC .............. A61B 17/7049; A61B 17/705; A61B 17/7052; Y10T 403/7041; Y10T 403/7105; Y10T 403/7129
(Continued)

(56) References Cited

U.S. PATENT DOCUMENTS

| | | | |
|---|---|---|---|
| 4,027,932 A | 6/1977 | Kunkel et al. | |
| 4,359,318 A | 11/1982 | Gittleman | |

(Continued)

FOREIGN PATENT DOCUMENTS

| | | |
|---|---|---|
| JP | 2011-139901 A | 7/2011 |
| JP | 2014-517739 A | 7/2014 |

(Continued)

*Primary Examiner* — Julianna N Harvey
*Assistant Examiner* — Christina Negrelli-Rodriguez
(74) *Attorney, Agent, or Firm* — Novick, Kim & Lee, PLLC; Sang Ho Lee

(57) ABSTRACT

A rod connector used in screw fixation to connect different rods includes a latch element including a latch section which is fitted to a first rod and a pass-through section having a through-hole, a support element including an up/down movement section which moves up and down through the through-hole and a support section which is a head part of the up/down movement section and has a support groove to support a second rod, and a fixing screw which approaches the up/down movement section through a screw hole formed in oblique direction within the latch element and presses the up/down movement section directly or indirectly, to fix the support element at a predetermined height.

6 Claims, 5 Drawing Sheets

(58) Field of Classification Search
USPC ............... 606/250–253, 260, 264–277, 278; 403/362, 385, 389
See application file for complete search history.

(56) References Cited

U.S. PATENT DOCUMENTS

| | | | |
|---|---|---|---|
| 4,474,516 A | 10/1984 | Schiefer | |
| 4,678,383 A | 7/1987 | Bergner | |
| 5,127,407 A | 7/1992 | Tan | |
| 5,265,504 A | 11/1993 | Fruhm | |
| 6,171,311 B1 * | 1/2001 | Richelsoph | A61B 17/7049 606/250 |
| 6,249,946 B1 | 6/2001 | Greenhill | |
| 6,258,089 B1 | 7/2001 | Campbell et al. | |
| 6,290,701 B1 | 9/2001 | Enayati | |
| 6,331,179 B1 | 12/2001 | Freid et al. | |
| 6,402,757 B1 | 6/2002 | Moore, III et al. | |
| 6,436,100 B1 | 8/2002 | Berger | |
| 6,652,525 B1 | 11/2003 | Assaker et al. | |
| 6,778,861 B1 | 8/2004 | Liebrecht et al. | |
| 7,029,472 B1 | 4/2006 | Fortin | |
| 7,194,314 B1 | 3/2007 | Richter et al. | |
| 7,235,100 B2 | 6/2007 | Martinek | |
| 7,302,298 B2 | 11/2007 | Lowry et al. | |
| 7,662,154 B2 | 2/2010 | Ribeiro | |
| 8,057,521 B2 | 11/2011 | Smisson, III et al. | |
| 8,419,777 B2 | 4/2013 | Walker et al. | |
| 8,454,667 B2 | 6/2013 | Humphreys | |
| 8,628,325 B2 | 1/2014 | Vachtenberg | |
| 8,758,347 B2 | 6/2014 | Weiner et al. | |
| 8,906,077 B2 | 12/2014 | Bush, Jr. et al. | |
| 8,932,335 B2 | 1/2015 | Humphreys | |
| 8,940,030 B1 | 1/2015 | Stein et al. | |
| 9,265,531 B2 | 2/2016 | Ziolo | |
| 9,629,664 B2 | 4/2017 | Altarac et al. | |
| 9,775,652 B2 | 10/2017 | Altarac et al. | |
| 9,918,749 B2 | 3/2018 | Altarac et al. | |
| 9,918,760 B2 | 3/2018 | Bush, Jr. et al. | |
| 2002/0151899 A1 | 10/2002 | Bailey et al. | |
| 2003/0187440 A1 | 10/2003 | Richelsoph et al. | |
| 2004/0220571 A1 | 11/2004 | Assaker et al. | |
| 2004/0243207 A1 | 12/2004 | Olson et al. | |
| 2004/0267361 A1 | 12/2004 | Donnelly et al. | |
| 2005/0059972 A1 | 3/2005 | Biscup | |
| 2005/0192577 A1 | 9/2005 | Mosca et al. | |
| 2005/0261689 A1 | 11/2005 | Lin | |
| 2006/0106390 A1 | 5/2006 | Jensen et al. | |
| 2006/0161157 A1 | 7/2006 | Mosca et al. | |
| 2006/0217721 A1 | 9/2006 | Suh | |
| 2006/0235410 A1 | 10/2006 | Ralph et al. | |
| 2006/0247639 A1 | 11/2006 | Anderson | |
| 2006/0293670 A1 | 12/2006 | Smisson et al. | |
| 2007/0233071 A1 | 10/2007 | Dewey et al. | |
| 2008/0161864 A1 | 7/2008 | Beck et al. | |
| 2008/0188897 A1 | 8/2008 | Krebs et al. | |
| 2008/0221624 A1 | 9/2008 | Gooch | |
| 2009/0125072 A1 | 5/2009 | Neubardt | |
| 2009/0318970 A1 | 12/2009 | Butler et al. | |
| 2010/0036467 A1 | 2/2010 | Kraus et al. | |
| 2010/0049256 A1 | 2/2010 | Jeon et al. | |
| 2010/0106198 A1 | 4/2010 | Adcox et al. | |
| 2010/0121383 A1 | 5/2010 | Stanaford et al. | |
| 2011/0022097 A1 | 1/2011 | Walker et al. | |
| 2011/0029023 A1 | 2/2011 | Tornier | |
| 2011/0106159 A1 | 5/2011 | Nazeck | |
| 2011/0144702 A1 | 6/2011 | Leroux et al. | |
| 2011/0152934 A1 * | 6/2011 | Asaad | A61B 17/7052 606/250 |
| 2011/0230885 A1 | 9/2011 | Weiner et al. | |
| 2011/0264151 A1 | 10/2011 | Davis et al. | |
| 2012/0185001 A1 | 7/2012 | Nayet et al. | |
| 2012/0232595 A1 | 9/2012 | Holschlag | |
| 2012/0265258 A1 | 10/2012 | Garvey | |
| 2012/0271363 A1 | 10/2012 | Luxon et al. | |
| 2012/0289978 A1 | 11/2012 | Jacob | |
| 2013/0023936 A1 | 1/2013 | Altarac et al. | |
| 2013/0041413 A1 | 2/2013 | Sun | |
| 2013/0231704 A1 | 9/2013 | Larroque-Lahitette | |
| 2013/0304067 A1 | 11/2013 | Hess et al. | |
| 2013/0325074 A1 | 12/2013 | Ziolo | |
| 2014/0066997 A1 | 3/2014 | Humphreys | |
| 2015/0134013 A1 | 5/2015 | Paul | |
| 2015/0201982 A1 | 7/2015 | Altarac et al. | |
| 2015/0216573 A1 | 8/2015 | Chin et al. | |
| 2015/0230838 A1 | 8/2015 | Lazoglu et al. | |
| 2016/0166295 A1 | 6/2016 | Ziolo | |
| 2016/0206351 A1 | 7/2016 | Eom | |

FOREIGN PATENT DOCUMENTS

| | | |
|---|---|---|
| KR | 1999-0035953 A | 5/1999 |
| KR | 10-2002-0082009 A | 10/2002 |
| KR | 1020040001287 A | 1/2004 |
| KR | 20-0367241 Y1 | 11/2004 |
| KR | 10-2005-0023111 A | 3/2005 |
| KR | 10-2007-0026472 A | 3/2007 |
| KR | 10-2007-0112200 A | 11/2007 |
| KR | 10-2008-0059920 A | 7/2008 |
| KR | 10-0850322 B1 | 8/2008 |
| KR | 10-2008-0105506 A | 12/2008 |
| KR | 10-0872529 B1 | 12/2008 |
| KR | 10-2009-0015933 A | 2/2009 |
| KR | 10-2009-0111774 A | 10/2009 |
| KR | 10-2010-0124709 A | 11/2010 |
| KR | 10-2012-0039622 A | 4/2012 |
| KR | 10-2012-0040309 A | 4/2012 |
| KR | 10-2012-0052265 A | 5/2012 |
| KR | 10-1142895 B1 | 5/2012 |
| KR | 10-2012-0057758 A | 6/2012 |
| KR | 10-2013-0004669 A | 1/2013 |
| KR | 10-2013-0015081 A | 2/2013 |
| KR | 10-2013-0016303 A | 2/2013 |
| KR | 10-1331429 B1 | 11/2013 |
| KR | 10-2014-0003938 A | 1/2014 |
| KR | 10-2014-0018796 A | 2/2014 |
| KR | 10-2014-0052320 A | 5/2014 |
| KR | 10-1413732 B1 | 7/2014 |
| KR | 10-2015-0120105 A | 10/2015 |
| WO | 2008/146981 A1 | 12/2008 |
| WO | 2009/105106 A2 | 8/2009 |

* cited by examiner

ROD CONNECTOR

TECHNICAL FIELD

The present disclosure relates to a rod connector, and more particularly, to a rod connector for connecting different rods simply and effectively.

BACKGROUND ART

In general, spine related diseases, can be treated by indirect methods utilizing physical therapy and direct methods by correcting and fixing the spine by installing a separate fixation device in the damaged part of the spine. That is, while minor spinal diseases can be treated by physical therapy, serious diseases in cervical, thoracic, lumbar and sacral regions and intervertebral discs that make up the spine are treated by using a separate spinal fixation device.

A spinal fixation device commonly used in surgery includes a pedicle (sacrum) screw which is inserted into the pedicle or sacrum of the vertebra at a predetermined angle and depth, a spinal rod disposed on one side of the spinal part, and a fixing cap or a fastener to fasten the spinal rod and the pedicle screw together, in order to correct the damaged part of the spine to normal condition and fix it without movement. To treat the damaged part of the spine, the pedicle screw is inserted and fixed into the pedicle or sacrum of the vertebra in optimum direction and position first, and then the spinal part is corrected to normal condition using the spinal rod, and the spinal rod and the fixing screw are fixed using the fixing cap or the fastener, and thus treatment is completed.

However, degeneration of the previous surgical site up and below requires re-surgery that is called symptomatic adjacent segment degeneration, and in such a case, it is necessary to connect an existing screw and a new screw, and since this process involves making an incision in the previous surgical site to replace the rod, it causes mental, physical and financial burdens for the patient. Recently, to solve this problem, a method (Korean Patent Application No. 10-2012-7000779) is proposed in which a connector is fitted to an existing rod and a new rod is connected to another hole of the connector; however, this method requires accurate 11-shaped arrangement of the rods due to the feature of the connector, that places limitations on the positional relationship between the rods, and since it is necessary to sufficiently remove the surrounding area of the rod, it causes problems where the surgery is still not easy and many burdens are imposed on the patient.

DISCLOSURE

Technical Problem

To solve the aforementioned problems, a need arises for a rod connector which allows easy connection of different rods to reduce a patient's physical burden during a surgery.

Ultimately, the present disclosure is directed to provide a rod connector that allows easy connection of an existing rod and a new rod that enables a surgery without removing much of the surrounding area of the existing rod, thereby reducing a patient's physical burden.

The objects intended to be solved by the present disclosure are not limited to the above-mentioned objects, and another object not mentioned herein will be clearly understood by those skilled in the art from the following disclosure.

Technical Solution

To achieve the object, a rod connector according to an embodiment of the present disclosure uses an internal screw fixation to connect different rods, and includes a latch element that utilizes a latch section where it is fitted to a first rod and a pass-through section having a through-hole, a support element including an up/down movement section which moves up and down through the through-hole, and a support section which is a head part of the up/down movement section that has a support groove to support a second rod, and a fixing screw which approaches the up/down movement section through a screw hole that forms in an oblique direction within the latch element and presses the up/down movement section directly or indirectly, to fix the support element at a predetermined height.

To achieve the object, a rod connector according to another embodiment of the present disclosure is a rod connector that is used in screw fixation to connect different rods, and includes a latch part which is fitted to a first rod, a support part formed above the latch part to support a second rod, and a connecting part connecting the latch part and the support part.

Advantageous Effects

According to the present disclosure, a rod connector can be provided that allows easy connecting of an existing rod and a new rod and enables surgery without removing much of the surrounding area of the existing rod, thereby reducing a patient's physical burden.

Figure 1:
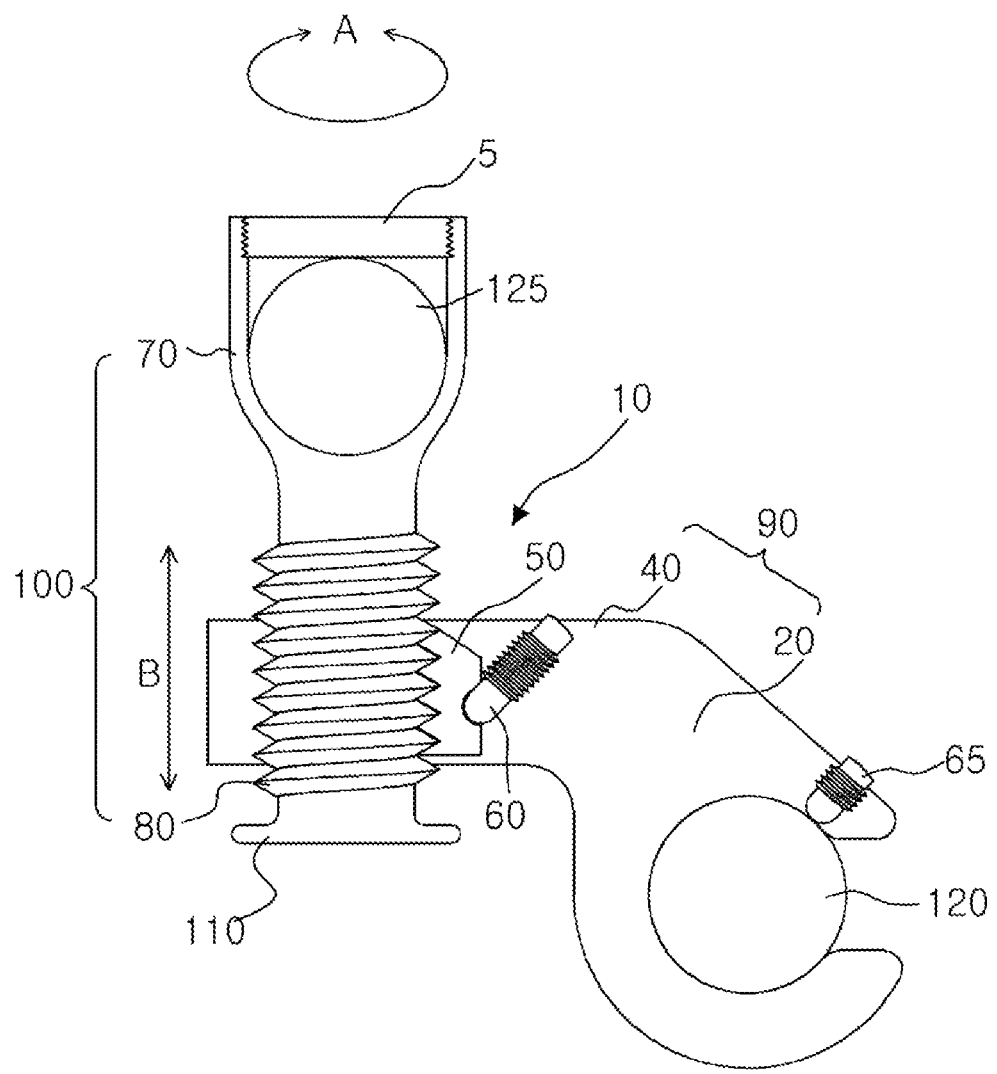
FIG. 1 is a diagram showing a rod connector according to an embodiment of the present disclosure.

| Detailed Description of Main Elements | |
|---|---|
| 10, 130, 190: Rod connector | 20, 140: Latch section |
| 25: Through-hole | 30: Screw hole |
| 35: Rod screw hole | 40, 150: Pass-through section |
| 50: Fixing piece | 55: Concave part |
| 60: Fixing screw | 65: Rod screw |
| 70, 175: Support section | |
| 80, 170: Up/down movement section | |
| 90, 160: Latch element | 100, 180: Support element |
| 110: Stop section | 120: First rod |
| 125: Second rod | 200: Latch part |
| 210: Support part | 220: Connecting part |

BEST MODE

Advantages and features of the present disclosure and methods for achieving them will be apparent from the embodiments described in details below with reference to the accompanying drawings. However, the present disclosure is not limited to the following disclosed embodiments and will be embodied in many different forms, that these embodiments are only provided to make the disclosure complete and help those having ordinary skill in the technical field pertaining to the present disclosure to understand the scope of the invention fully, and the present disclosure is only defined by the scope of the appended claims. Same reference numerals indicate same elements throughout the specification.

The terminology used herein is only for the purpose of describing the embodiments and is not intended to limit the present disclosure. As used herein, the singular forms are intended to include the plural forms as well, unless the context clearly indicates otherwise. The term "comprises" and/or "comprising" when used in this specification specify the presence of stated elements, steps and operations, but do not preclude the presence or addition of one or more other elements, steps and operations.

Figure 2:
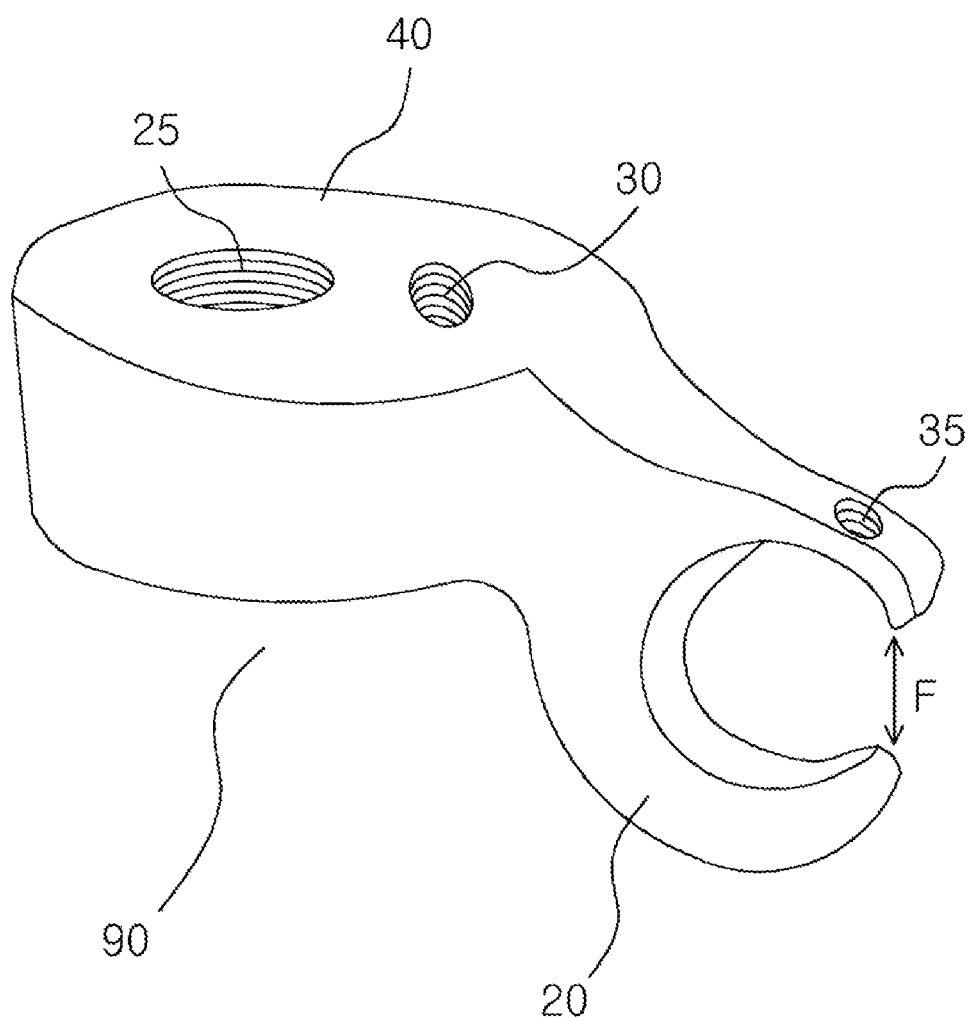
FIG. 2 is a schematic perspective view of a latch element of a rod connector according to an embodiment of the present disclosure.
Figure 3A:
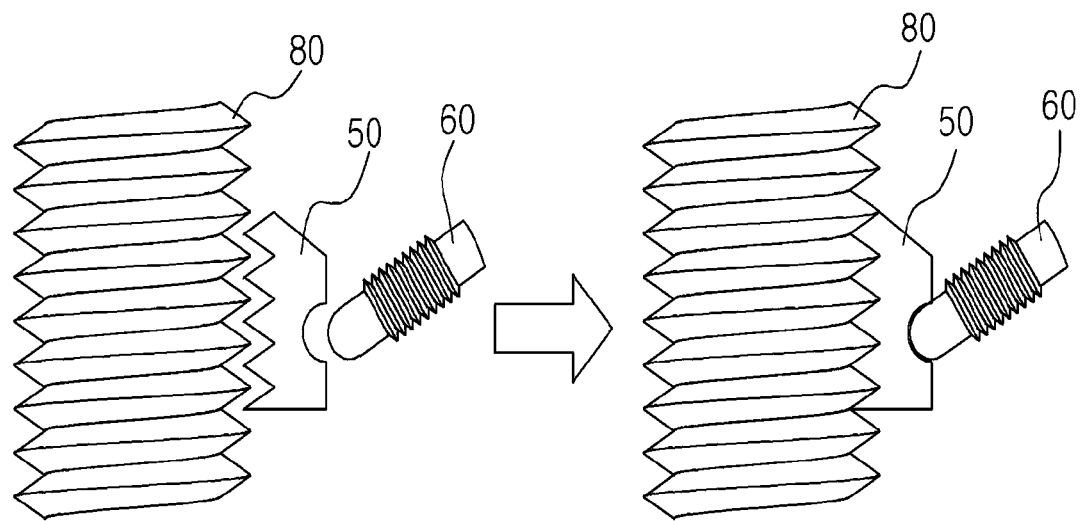
FIGS. 3A and 3B are diagrams showing a process of fixing the position of a support element of a rod connector according to an embodiment of the present disclosure.
Figure 3B:
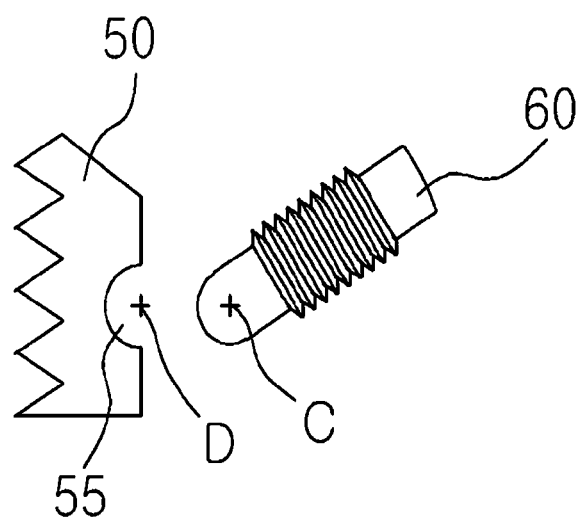

A rod connector according to an embodiment of the present disclosure is described in FIGS. 1 to 3B. FIG. 1 is a diagram showing the rod connector according to an embodiment of the present disclosure. FIG. 2 is a schematic perspective view of a latch element of the rod connector according to an embodiment of the present disclosure. FIGS. 3A and 3B are diagrams showing a process of fixing the position of a support element of the rod connector according to an embodiment of the present disclosure.

Referring to FIGS. 1 to 3B, the rod connector 10 according to an embodiment of the present disclosure is an element that is used in screw fixation to connect different rods, and includes a latch element 90, a support element 100, a fixing piece 50, a fixing screw 60 and a rod screw 65.

The latch element 90 is an element that is fitted to a first rod 120 and includes a latch section 20 that is fitted to the first rod 120 and a pass-through section 40 having a through-hole 25. In the case of the degeneration of previous surgical site up and below using screw fixation, also known as symptomatic adjacent segment degeneration, which requires re-surgery, it is necessary to connect an existing screw previously fixed in the bone and a new screw, and to do so, it is necessary to connect a rod (i.e., the first rod 120) that supports the existing screw and a rod (i.e., a second rod 125) that supports the new screw. To connect different rods, first, the latch section 20 of the latch element 90 is capable of fitting to the first rod 120.

The latch section 20 of the latch element 90 may have a hook shape with an open part F which is not a closed type, and as a result, to connect the latch element 90 and the existing first rod 120, it is not necessary to loosen the existing screw, but only requires to fit the latch section 20 in between screws of the first rod or another part of the first rod 120. As a result, the surgery can be simplified, and reduces operation time and patient's physical and mental burdens.

The pass-through section 40 of the latch element 90 has the through-hole 25, and the support element 100 as described below can make upward and downward motion B through the through-hole 25. The through-hole 25 may have a thread on the surface thereof and the support element 100 may have a thread as well, and thus the support element 100 may make upward and downward motion B while rotating A by screw coupling of the thread of the through-hole 25 and the thread of the support element 100.

In addition to the through-hole 25, the pass-through section 40 can have a screw hole 30 into which the fixing screw 60 is inserted to fix the position of the support element 100. The screw hole 30 can be formed in oblique direction within the pass-through section 40, and the fixing screw 60 can be moved to the support element 100 in oblique direction in engagement with the thread of the screw hole 30.

The support element 100 supports the second rod 125, and includes an up/down movement section 80 that may move up and down through the through-hole 25 of the latch element 90 and a support section 70 that is a head part of the up/down movement section 80 and has a support groove to support the second rod 125, and additionally, a thread is formed on the inner surface of the support section 70, and as a fixing bolt 5 is tightened into the thread, the second rod 125 can be fixed to the support section 70. Specifically, the up/down movement section 80 has a thread on the surface thereof as well as the through-hole 25 of the latch element 90 has the thread as well, and thus the up/down movement section 80 can make upward and downward movement B through rotation A by screw that couples with the through-hole 25. Furthermore, through this upward and downward movement B, the height of the support element 100 can be adjusted, allowing easy support of the second rod 125, and as a result, the rod connector 10 can easily connect the first rod 120 and the second rod 125, thereby simplifying the surgery and reducing the patient's burden.

Additionally, a stop section 110 with a width that is longer than the maximum width of the through-hole 25 is formed below the up/down movement section 80, and even if the up/down movement section 80 moves up, it can prevent the support element 100 from slipping out of the latch element 90. Of course, in some instances, the stop section 110 can be absent, and in this case, the support element 100 may be separated from the latch element 90.

The support section 70 of the support element 100 is a head part of the up/down movement section 80 and has the support groove to support the second rod 125, where the second rod 125 is seated in the support groove, and because the thread is formed on the inner surface of the support section 70, as the fixing bolt 5 is tightened into the thread, the second rod 125 can be fixed to the support section 70. Accordingly, as the first rod 120 is fitted in the latch element 90 and the second rod 125 is fixed to the support element 100, the rod connector 10 including the latch element 90 and the support element 100 connects the first rod 120 and the second rod 125.

The fixing piece 50 is an element that is disposed adjacent to the up/down movement section 80 of the support element 100 inside the latch element 90 and presses the thread of the up/down movement section 80 in close contact with the thread to fix the support element 100 at a height that is easy to connect the first rod 120 and the second rod 125. Specifically, the fixing piece 50 can be disposed within the latch element 90 adjacent to the through-hole 25 of the latch element 90, and a thread may be formed on one end surface of the fixing piece 50 and protrude toward the through-hole 25, forming a partial surface of the through-hole 25, and a spherical concave part 55 can be formed on the other end surface of the fixing piece 50.

Furthermore, when the fixing screw 60 pushes and presses the spherical concave part 55 of the fixing piece 50, the fixing piece 50 moves to the through-hole 25 and comes close contact with the thread of the up/down movement section 80 of the support element 100, and as a result, the support element 100 cannot move up and down and may be fixed at an intended predetermined height.

The fixing screw 60 is an element that fixes the support element 100 at a predetermined height through the screw hole 30 that is formed in an oblique direction within the latch element 90, and specifically, the pass-through section 40 of the latch element 90 can have the screw hole 30 into which the fixing screw 60 is inserted, the screw hole 30 can be formed in oblique direction toward the through-hole 25 inwards from the outer surface of the pass-through section 40, and the fixing screw 60 can move in oblique direction in engagement with the thread of the screw hole 30. Furthermore, the end part of the fixing screw 60 that contacts with the fixing piece 50 is spherical, and when the fixing screw 60 is tightened, the spherical end part comes into contact with the spherical concave part 55 of the fixing piece 50 and pushes the fixing piece 50 against the through-hole 25. As a result, the thread of the pushed fixing piece 50 comes into close contact with the thread of the up/down movement section 80 of the latch element 90, limiting the upward and downward movement of the latch element 90.

To the same extent, when the spherical end part of the fixing screw 60 and the concave part 55 of the fixing piece 50 are brought into contact, the center C of the spherical end part of the fixing screw 60 and the center D of the spherical concave part 55 of the fixing piece 50 can be matched, and accordingly, all points on the surface of the sphere are at the same distance from the center of the sphere, and thus the pressing force of the fixing screw 60 is applied to all the points on the concave part 55 of the fixing piece 50 and the applied force acts equally on all the points. That is, although the fixing screw 60 obliquely enters the fixing piece 50, the pressing force by the fixing screw 60 can act equally on all the points of the concave part 55 of the fixing piece 50, and accordingly, the fixing piece 50 approaches without deflection and comes into close contact with the up/down movement section 80 of the latch element 90, thereby effectively preventing the movement of the latch element 90.

As noted above, it is possible to easily adjust the height of the support element 100 through interaction between the fixing screw 60 and the fixing piece 50, and, therefore easily connect the existing rod and the new rod, thereby simplifying the surgery process and reducing the patient's physical burden.

Additionally, the rod connector 10 according to an embodiment of the present disclosure can include the rod screw 65, and the rod screw 65 can press the first rod 120 against the latch section 20 of the latch element 90 so that the first rod 120 is fixed to the latch section 20 of the latch element 90 to keep the first rod 120 from moving. That is, after the latch element 90 is fitted to the first rod 120, the rod screw 65 is tightened through a rod screw hole 35 and presses the first rod 120 against the latch element 90, thereby preventing the movement of the first rod 120. As the rod screw 65 prevents the movement of the first rod 120 as described above, it is possible that the first rod 120 can prevent the rod connector 10 from slipping out.

The rod connector according to an embodiment of the present disclosure has been hereinabove described, and a rod connector according to another embodiment of the present disclosure is hereinafter described.

Figure 4:
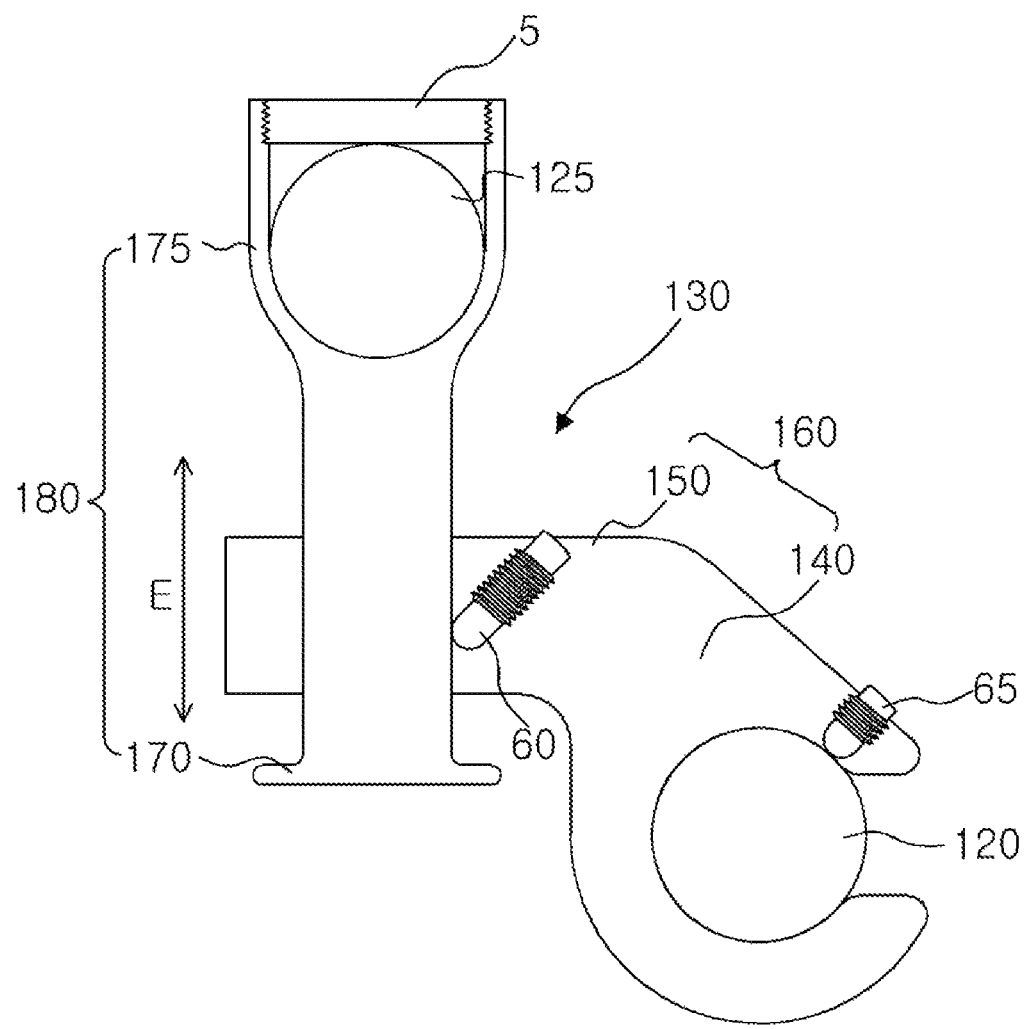
FIG. 4 is a diagram showing a rod connector according to another embodiment of the present disclosure.

The rod connector according to another embodiment of the present disclosure is described with reference to FIG. 4. FIG. 4 is a diagram showing the rod connector according to another embodiment of the present disclosure.

Referring to FIG. 4, as opposed to the above-described rod connector 10 according to an embodiment of the present disclosure, the rod connector 130 according to another embodiment of the present disclosure has no thread on an up/down movement section 170 of a support element 180 and a through-hole and has no fixing piece, and thus the fixing screw 60 does not pass through the fixing piece and directly presses the up/down movement section 170 to limit the upward and downward movement of the support element 180.

The up/down movement section 170 of the support element 180 can make upward and downward movement E through a through-hole of a latch element 160, and when a support section 175 of the support element 180 is determined to be at a proper height for supporting the second rod 125, the up/down movement section 170 stops moving, and the fixing screw 60 is tightened and presses the up/down movement section 170, so the support element 180 can be fixed at a predetermined height. Furthermore, the support section 175 has a thread on the inner surface thereof, and as the fixing bolt 5 is tightened into the thread, the second rod 125 can be fixed to the support section 175.

On the same side, the rod connector 130 according to another embodiment of the present disclosure does not need to form the threads on the up/down movement section 170 and the through-hole and does not require the fixing piece, and thus the benefit is that it is simple and convenient for manufacturing and maintenance.

The rod connector according to another embodiment of the present disclosure has been hereinabove described, and a rod connector according to still another embodiment of the present disclosure is hereinafter described.

Figure 5:
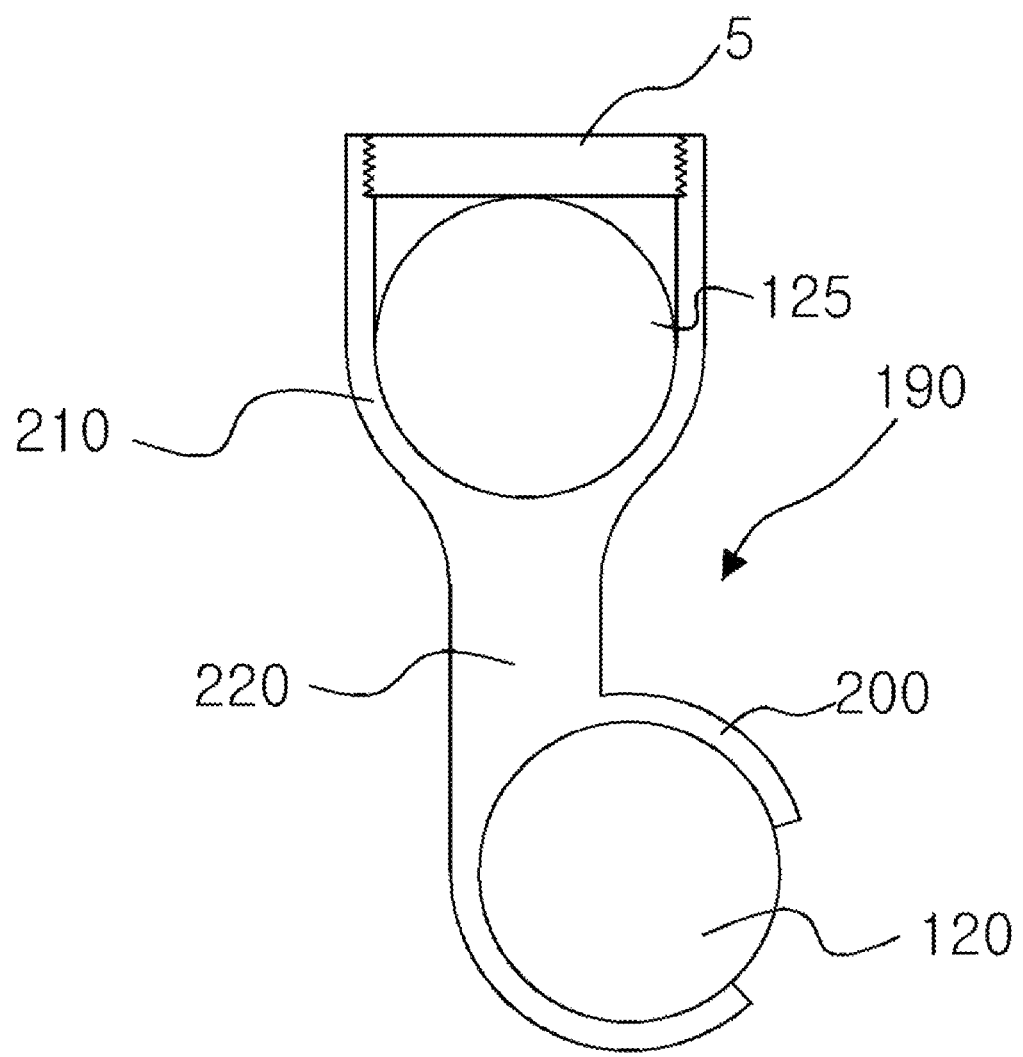
FIG. 5 is a diagram showing a rod connector according to still another embodiment of the present disclosure.

The rod connector according to still another embodiment of the present disclosure is described with reference to FIG. 5. FIG. 5 is a diagram showing the rod connector according to still another embodiment of the present disclosure.

Referring to FIG. 5, the rod connector 190 according to still another embodiment of the present disclosure may have the latch element and the support element formed integrally, as opposed to the above-described rod connectors 10 and 130. Specifically, the rod connector 190 according to still another embodiment of the present disclosure can include a latch part 200 that may be fitted to the first rod 120, a support part 210 formed above the latch part 200 to support the second rod 125, and a connecting part 220 that connecting the latch part 200 and the support part 210. Furthermore, the support part 210 has a thread on the inner surface thereof, and as the fixing bolt 5 is tightened into the thread, the second rod 125 can be fixed to the support part 210.

To the same extent, the rod connector 190 according to still another embodiment of the present disclosure has simple manufacturing process and cost saving effects due to being formed as one element, as opposed to the above-described rod connectors 10 and 130.

While the embodiments of the present disclosure have been hereinabove described with reference to the accompanying drawings, it will be appreciated by those having ordinary skill in the technical field pertaining to the present disclosure that the present disclosure can be embodied in other specific forms without changing the technical spirit or essential features of the present disclosure. Therefore, it should be understood that the embodiments described above are for illustration purposes only in all aspects, but not intended to be limiting.

The invention claimed is:

1. A rod connector used in screw fixation to connect different rods, the rod connector comprising:
   a latch including a latch section configured to hold a first rod, and a pass-through section having a through-hole;
   a support assembly including an up-and-down movement section configured to move up and down through the through-hole, and a support section connected to the up-and-down movement section and having a support groove to support a second rod; and a fixing screw configured to approach the up-and-down movement section through a screw hole disposed in the latch, a fixing piece configured to hold and fix the support assembly at the predetermined height by a close contact between the fixing piece and the up-and-down movement section by a pushing force of the fixing screw.

2. The rod connector of claim 1, wherein the latch section has a rod screw hole, and the rod connector further comprises a rod screw to hold the first rod through the rod screw hole.

3. The rod connector of claim 1, wherein threads are defined on a surface of the up-and-down movement section and an inner circumferential surface of the through-hole.

4. The rod connector of claim 1, wherein an end part of the fixing screw which contacts the fixing piece has a spherical shape, and a part of the fixing piece which contacts the spherical shape of the end part of the fixing screw has a spherical concave shape, and when the fixing screw and the fixing piece are brought into contact, a center of the spherical shape of the end part of the fixing screw and a center of the spherical concave shape of the part of the fixing piece match one another.

5. The rod connector of claim 1, wherein a stopper is disposed below the up-and-down movement section, and the stopper has a width that is larger than a maximum width of the through-hole.

6. The rod connector of claim 1, wherein the support section has threads on an inner surface thereof, and when a fixing bolt is tightened into the threads, the second rod is held and fixed to the support section.

* * * * *